United States Patent [19]

McConnell et al.

[11] Patent Number: 5,496,950
[45] Date of Patent: Mar. 5, 1996

[54] USE FOR BIS-HETEROCYCLIC COMPOUNDS AND PHARMACEUTICAL COMPOSITIONS CONTAINING SAME

[75] Inventors: Oliver J. McConnell, Vero Beach, Fla.; Gabriel Saucy, Essex Fells, N.J.; Robert Jacobs, Santa Barbara, Calif.; Sarath P. Gunasekera, Vero Beach, Fla.

[73] Assignee: Harbor Branch Oceanographic Institution, Inc., Fort Pierce, Fla.

[21] Appl. No.: 330,651

[22] Filed: Oct. 28, 1994

Related U.S. Application Data

[60] Division of Ser. No. 201,309, Feb. 24, 1994, which is a continuation-in-part of Ser. No. 21,929, Feb. 24, 1993, Pat. No. 5,290,777.

[51] Int. Cl.$^6$ ............... C07D 241/02; C07D 403/02; C07D 241/04; A61K 31/495

[52] U.S. Cl. ............... 544/408; 544/373; 544/384; 548/312.1

[58] Field of Search ............................. 544/408

[56] References Cited

U.S. PATENT DOCUMENTS

| 4,866,084 | 9/1989 | Gunasekera et al. | 514/397 |
| 4,895,844 | 1/1990 | Komoto et al. | 514/254 |
| 4,970,226 | 11/1990 | Sun et al. | 514/254 |

OTHER PUBLICATIONS

Faulkner, D. J. (1984) "Marine Natural Products: Metabolites of Marine Invertebrates" Natural Products Reports 1:551–598.
Faulkner, D. J. (1986) "Marine Natural Products" Natural Products 3:1–33.
Faulkner, D. J. (1987) "Marine Natural Products" Natural Products Reports 4(5):539–576.
Uemura, D. et al. (1985) "Norhalichondrin A: An Antitumor Polyether Macrolide from a Marine Sponge" J. Am. Chem. Soc. 107:4796–4798.
Moquin, C., M. Guyot (1984) "Grossularine, A Novel Indole Derivative from the Marine Tunicate, *Dendrodoa grossularia*" Tetrahedron Letters 25(44):5047–5048.
Norton, R. S., R. J. Wells (1982) "A Series of Chiral Polybrominated Biindoles from the Marine Blue–Green Alga *Rivularia firma*. Application of $^{13}$C NMR Spin–Lattice Relaxation Data and $^{13}$C–$^1$H Coupling Constants to Structure Elucidation" J. Am. Soc. 104(13):3628–3635.

Primary Examiner—Cecilia Tsang
Attorney, Agent, or Firm—Saliwanchik & Saliwanchik

[57] ABSTRACT

A novel use for the class of biologically active bis-heterocyclic, e.g., bis-indole alkaloid compounds, which have been named topsentins, nortopsentins, hamacanthins, or dragmacidins, pharmaceutical compositions containing them, methods of producing the compounds, and methods of using the compounds are disclosed. Specifically, the novel utility pertains to the anti-inflammatory properties exhibited by the bis-indole compounds and their analogs.

3 Claims, 3 Drawing Sheets

USE FOR BIS-HETEROCYCLIC COMPOUNDS AND PHARMACEUTICAL COMPOSITIONS CONTAINING SAME

CROSS-REFERENCE TO A RELATED APPLICATION

This is a division of application Ser. No. 08/201,309, filed Feb. 24, 1994, allowed which is a continuation in part of application Ser. No. 08/021,929, filed Feb. 24, 1993, now U.S. Pat. No. 5,290,777.

FIELD OF THE INVENTION

This application relates to compounds which are used as anti-inflammatory agents and compositions containing such compounds as active ingredients. More particularly, the invention concerns a novel use of biologically active his-heterocyclic compounds, e.g., bis-indoles, pharmaceutical compositions containing these compounds, and methods of producing the compounds. The novel use of the compounds relates to the anti-inflammatory properties of the disclosed bis-heterocyclic compounds, which include the bis-indoles known as topsentins, nortopsentins, dragmacidins, and their analogs and derivatives.

BACKGROUND OF THE INVENTION

The prevention and control of inflammation is of prime importance to man, and much research has been devoted to development of compounds having anti-inflammatory properties. Certain methods and chemical compositions have been developed which aid in inhibiting or controlling inflammation, but additional methods and anti-inflammatory compositions are needed.

It has been found that some natural products and organisms are potential sources for chemical molecules having useful biological activity of great diversity. Marine sponges have proved to be such a source, and a number of publications have issued disclosing organic compounds derived from marine sponges. Such publications include Scheuer, P. J., Ed. (1978–1983) *Marine Natural Products, Chemical and Biological Perspectives,* Academic Press, New York; Faulkner, D. J. (1984) *Natural Products Reports* 1:551–598; Faulkner, D. J. (1986) *Natural Products Reports* 3:1–33; Faulkner, D. J. (1987) *Natural Products Reports* 4:539–576; Uemura, D., K. Takahashi, T. Yamamoto, C. Katayama, J. Tanaka, Y. Okumura, Y. Hirata (1985) *J. Am. Chem. Soc.* 107:4796–4798.

Indole compounds of marine origin have also been described in Moquin, C., M. Guyot (1984) *Tetrahedron Letters* 25(44):5047–5048 and Norton, R. S., R. J. Wells (1982) J. Am. Chem. Soc. 104(13):3628–3635.

Utilizing sponges as a source material and supplemented by novel synthetic production methods, new classes of biologically active compounds and new pharmaceutical compositions useful as antitumor and antiviral agents have been provided to the art. See U.S. Pat. Nos. 4,866,084, 4,895,844, and 4,970,266. The present invention provides a novel utility for these and related compounds, namely as anti-inflammatory compositions.

Other advantages and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

BRIEF SUMMARY OF THE INVENTION

The objects of the invention are accomplished by the provision of a novel utility for the class of biologically active bis-heterocyclic compounds that have a general structure according to the formula:

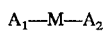

wherein $A_1$ and $A_2$ can be a heterocycle; and M is a core moiety linking the heterocycles, $A_1$ and $A_2$. Typically, the compound comprises an indole as the $A_1$ and $A_2$ moieties. Thus, the compound can be a bis-indole. The bis-indoles can be topsentins, nortopsentins, dragmacidins, and salts, analogs, or derivatives thereof. Other compounds of the subject invention can comprise a pyridyl as the $A_1$ and $A_2$ moieties, thus forming a bis-pyridine.

As embodied and fully described herein, the invention also comprises pharmaceutical compositions, e.g., anti-inflammatory compositions, containing as active ingredient an effective amount, preferably between about 0.1 to 45%, especially 1 to 25%, by weight based on the total weight of the composition, of one or more compounds according to the formulas expressed above and a non-toxic, pharmaceutically acceptable carrier or diluent. In addition, a pharmaceutical composition can comprise at least one of the subject bis-indole compounds and a second component comprising at least one other anti-inflammatory compounds. Such other anti-inflammatory compounds include, but are not limited to, steroidal compounds, e.g., hydrocortisone and the like; non-steroidal anti-inflammatories, e.g., acetylsalicylic acid (aspirin), ibuprofen, acetaminophen, indomethacin, and the like.

As embodied and fully described herein, the invention comprises processes for the production of compounds and compositions of the invention and novel methods of use thereof, e.g., methods of inhibiting an inflammatory response in an animal.

In accordance with the invention, methods for inhibiting inflammation comprise administering to the animal in need of such treatment an effective amount of the pharmaceutical compositions of the invention.

DETAILED DISCLOSURE OF THE INVENTION

Figure 1:
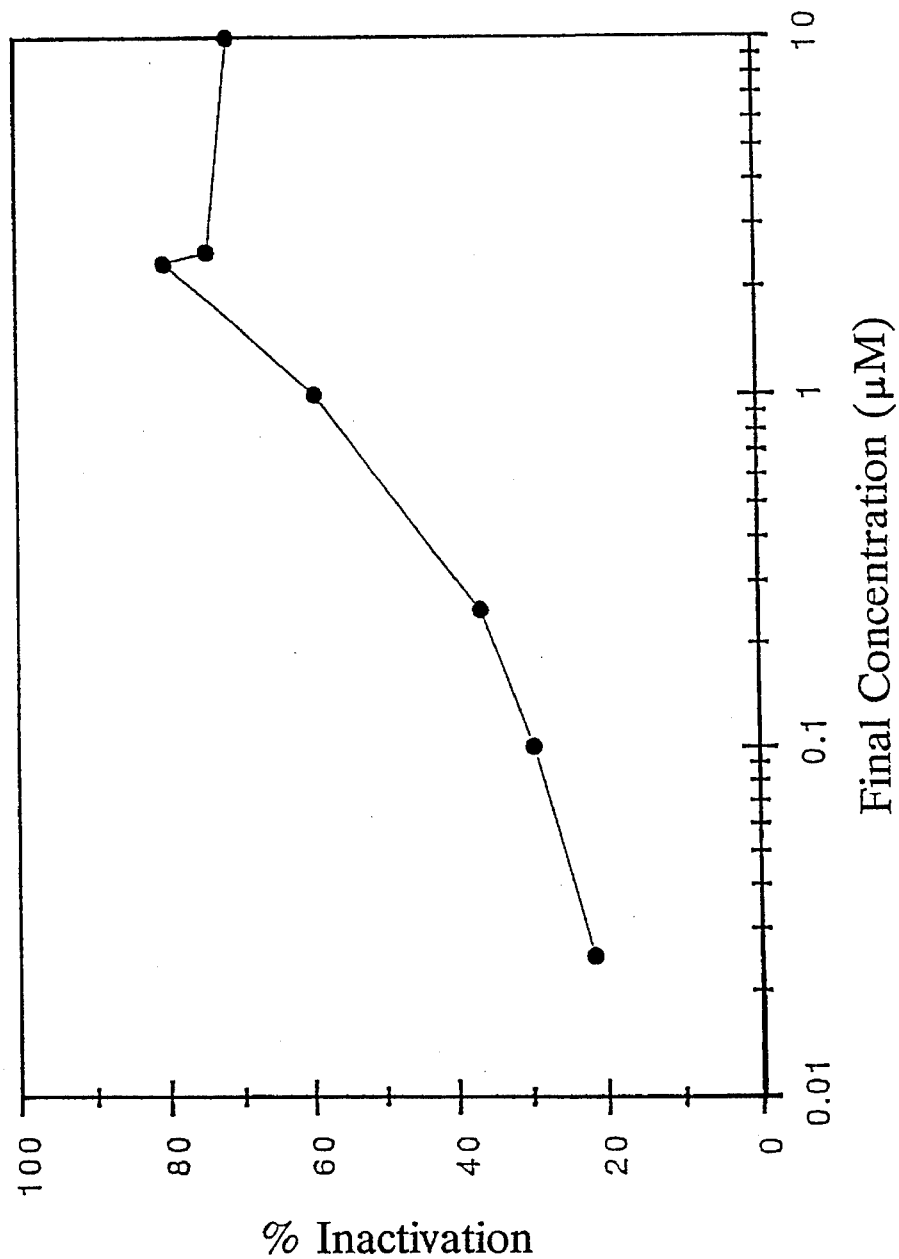
FIG. 1 shows the dose response for topsentin (HB18), as measured by percent inactivation of bee venom phospholipase A2.

A more complete understanding of the invention can be obtained by reference to preferred embodiments of the invention, which are illustrated by the following specific examples of compounds, compositions, and methods of the invention. It will be apparent to those skilled in the art that the examples involve use of materials and reagents that are commercially available from known sources, e.g., chemical supply houses, so no details are given respecting them.

The subject invention pertains to a novel use as an anti-inflammatory agent of bis-heterocyclic compounds and compositions comprising the bis-heterocyclic compounds. The subject compounds, some of which are also novel, comprise a chemical of the general formula:

wherein $A_1$ and $A_2$ are a heterocycle; and M is a core moiety linking the heterocycles, $A_1$ and $A_2$. These heterocycles, $A_1$ and $A_2$, can be the same or different, but are preferably the same. The heterocycles $A_1$ and $A_2$ can be indole, pyridine, pyrimidine, purine, pyrrole, furan, theophene, imidazole, benzimidazole, oxazole, thiazole, pyrazole, 3-pyrroline, pyrrolidine, quinolone, isoquinolone, carbazole, cyclic anhydride, cyclic imide, lactone, and the like. The heterocycles can be linked to the core group at any position on the heterocyclic ring. When the core moiety is a ring structure, the heterocyclic rings $A_1$ and $A_2$ can be linked thereto at any position on the core moiety. The specific bond position for any particular compound of the subject invention would be apparent to an ordinarily skilled artisan. Substitutions and additions to the heterocycles are also readily recognized by those persons of ordinary skill in the organic chemical arts.

The core moiety, M, linking the heterocycles, can be a cyclic or acyclic group comprising at least three atoms. The core moiety can comprise an acyclic chain having C, H, N, O, or S atoms. For example, M can be the core group

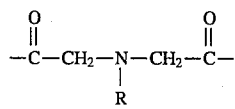

wherein R is a C1–C8 alkyl or alkoxyl group. A condensation reaction with this group yields the heterocycle:

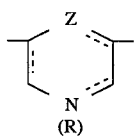

wherein Z=C, N, O, or S; and R=C1–C8 alkyl or alkoxyl group. Other heterocycles which can be used as the core group for compounds used in the subject invention are known to, and easily recognized by, those of ordinary skill in the art. As with the heterocycles discussed above, ordinarily skilled chemists would recognize that when the core moiety is a cyclic structure, the bonds to the heterocycles can be at any position of the core ring. These other core group heterocycles include:

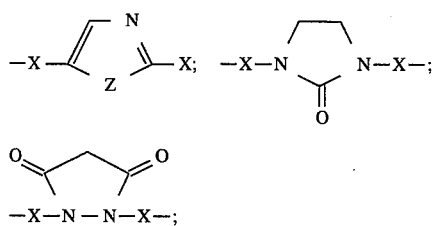

and the like, wherein X can be present or absent and can be an organic moiety, e.g., any lower alkyl or lower alkoxyl, or an inorganic molecule which can bond to the core group and the bis-heterocycles of the compound; and Z can be C, N, O, or S. A preferred embodiment of the subject invention is a bis-indole compound, wherein the indoles can be linked to the core group at the 2- or 3- positions of the indoles. One preferred embodiment includes a bis-indole compound wherein both indoles are linked to the core group at the 3-position. This preferred embodiment is shown below as the structure:

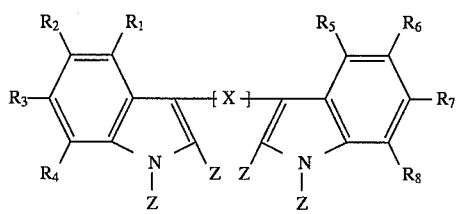

wherein X=an acyclic or a heterocyclic moiety selected from the group consisting of:

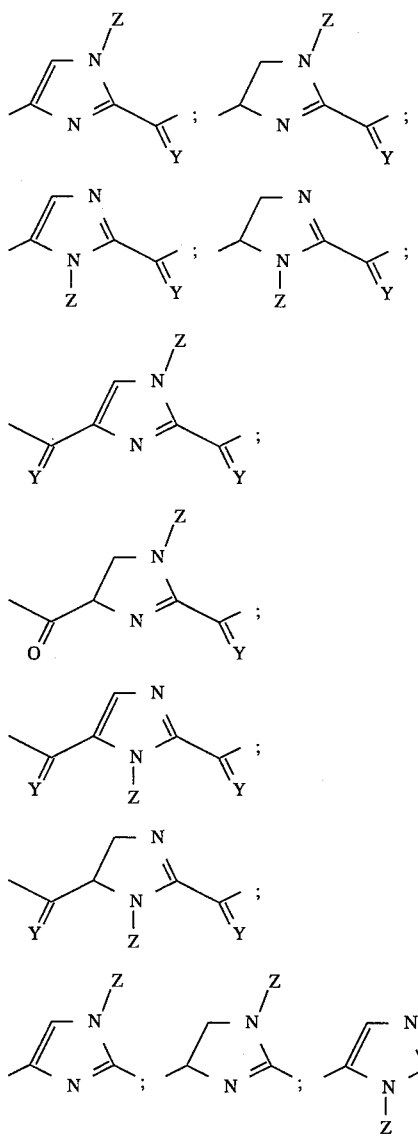

-continued

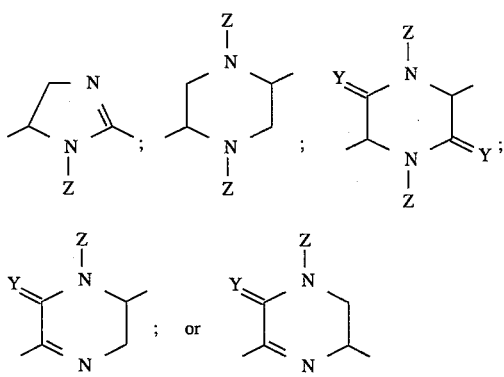

$R_{1-8}$ are the same or different selected from —H, —OH, halogen, —R, —OR, —OCOR, or —OA;

Y is the single group =O, or two groups, same or different, selected from —H, —OH, —OR, or —OCOR;

Z is independently selected from —H, —R, or —COR;

R is C1–8 alkyl or C1–8 alkoxyl; and A is —R-phenyl.

A preferred group of compounds of the invention are those of the formula:

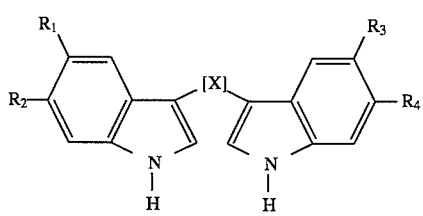

wherein X=

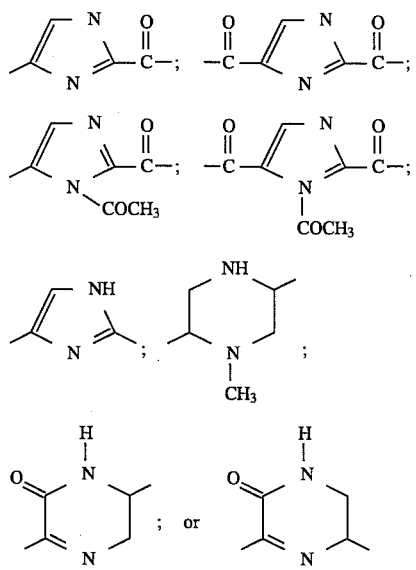

and wherein $R_1$ and $R_3$ are —H while $R_2$ and $R_4$ are —H, —OH, halogen, —R, —OR, —OCOR, or —OA; or $R_2$ and $R_4$ are —H while $R_1$ and $R_3$ are —H, —OH, halogen, —R, —OR, —OCOR, or —OA; R is C1–5 alkyl and A is —R-phenyl.

Particularly preferred compounds of the invention are those of the formulae:

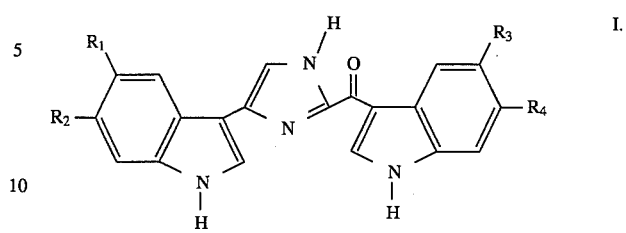
I.

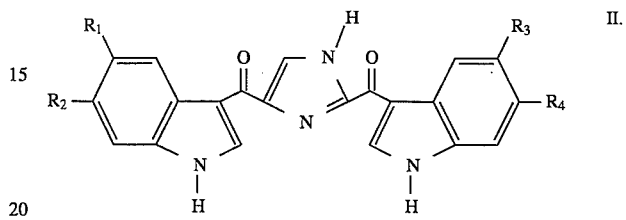
II.

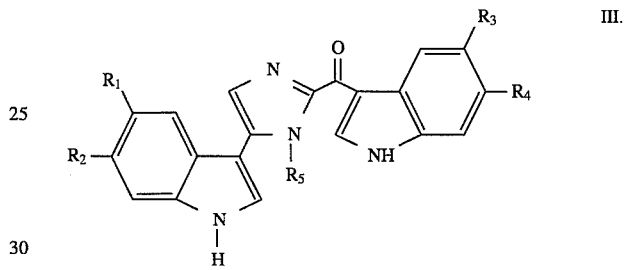
III.

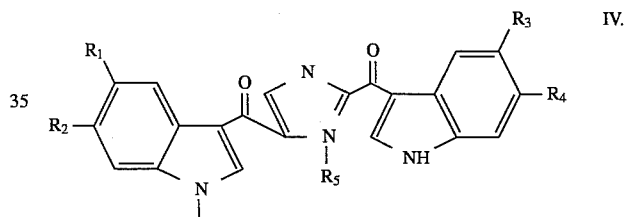
IV.

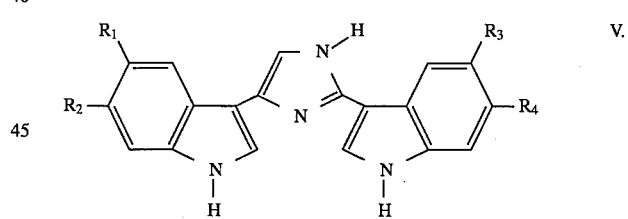
V.

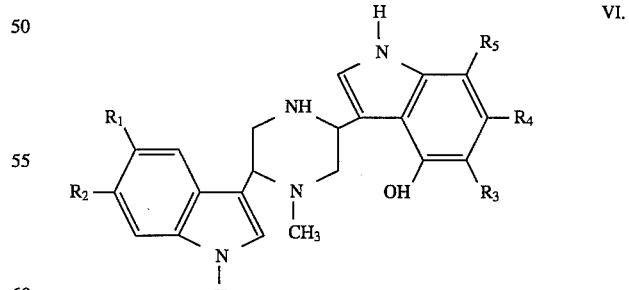
VI.

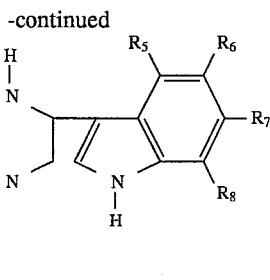

VII.

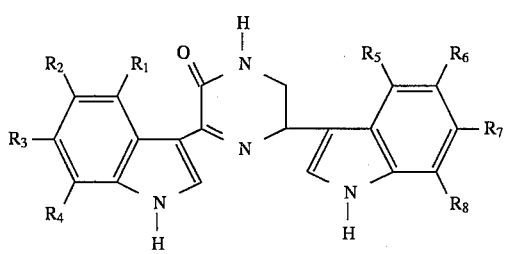

VIII.

wherein:

I(a): $R_1$, $R_2$, $R_3$=H; $R_4$=OH (Topsentin)

I(b): $R_1$, $R_3$=H; $R_2$=Br; $R_4$=OH (Bromotopsentin)

I(c): $R_1$, $R_3$, $R_4$=H; $R_2$=OH (Isotopsentin)

I(d): $R_1$, $R_3$=H; $R_2$, $R_4$=OH (Hydroxytopsentin)

I(e): $R_1$, $R_2$, $R_3$, $R_4$=H (Deoxytopsentin)

I(f): $R_1$, $R_2$, $R_4$=H; $R_3$=OH (Neotopsentin)

I(g): $R_2$, $R_3$, $R_4$=H; $R_1$=OH (Neoisotopsentin)

I(h): $R_1$, $R_3$=OH; $R_2$, $R_4$=H (Neohydroxytopsentin)

II(j): $R_1$, $R_2$, $R_3$=H; $R_4$=OH (Homocarbonyltopsentin)

III(k): $R_1$, $R_2$, $R_3$, $R_5$=H; $R_4$=OCOCH$_3$ (Topsentin monoacetate)

III(l): $R_1$, $R_2$, $R_3$=H; $R_4$=OCOCH$_3$; $R_5$=COCH$_3$ (Topsentin diacetate)

IV(m): $R_1$, $R_2$, $R_3$, $R_5$=H; $R_4$=OCOCH$_3$ (Homocarbonyltopsentin monoacetate)

V(n): $R_1$, $R_3$=H; $R_2$, $R_4$=Br (Nortopsentin A)

V(o): $R_1$, $R_2$, $R_3$=H; $R_4$=Br (Nortopsentin B)

V(p): $R_1$, $R_3$, $R_4$=H; $R_2$=Br (Nortopsentin C)

VI(q): $R_1$, $R_3$=H; $R_2$, $R_4$, $R_5$=Br (Dragmacidin)

VII(r): $R_1$, $R_2$, $R_4$, $R_5$, $R_6$, and $R_8$=H; $R_3$ and $R_7$=Br (Hamacanthin A)

VIII(s): $R_1$, $R_2$, $R_4$, $R_5$, $R_6$, and $R_8$=H; $R_3$ and $R_7$=Br (Hamacanthin B)

Bis-indole compounds have been previously described as having antimicrobial, antitumor, or antiviral activity. The topsentins are disclosed in U.S. Pat. No. 4,866,084. Dragmacidin and its related compounds isolated from the marine sponge of the Dragmacidon sp. are disclosed in U.S. Pat. No. 4,895,844. Similarly, the nortopsentins have been disclosed in U.S. Pat. No. 4,970,226. These patents are herein incorporated by reference.

The hamacanthins have not been previously disclosed. These hamacanthin compounds were exemplified herein as Formulae VII and VIII. The hamacanthins were isolated from a new species of Hamacantha sponge (phylum Porifera, class Demospongiae, order Poecilosclerida, family Biemnidae) collected by the Johnson-Sea-Link I manned submersible from a sand slope at a depth of 548 m off the southeast coast of Madiera (latitude 32°42.41'N, longitude 60°40.25'W). In life, the sponge was amorphous and yellow-white in color. A taxonomic voucher specimen is deposited in the Harbor Branch Oceanographic Museum (catalog no. 003:00920, DMBR no. 27-V-91-3-003). The hamacanthins have shown antifungal properties, e.g., efficacy against Candida albicans. Anti-inflammatory activity for the hamacanthins has now been discovered. The extraction procedure for obtaining the hamacanthins from sponge, as well as chemical characterization of the compounds hamacanthin A and hamacanthin B, are described below in Example 4.

Skilled chemists will be able to use procedures as disclosed herein and others to synthesize these compounds from available stock substances. In carrying out such operations, any suitable filtration, chromatographic, and other purification techniques include reversed phase, medium pressure, and high pressure liquid chromatography (RPLC, MPLC, and HPLC, respectively) with a suitable column as would be known to those skilled in the art, including silica gel, Sephadex LH-20, ammonia-treated silica gel, and LiChrosorb NH$_2$ columns. Such columns are eluted with suitable elements such as heptane, ethyl acetate, methylene chloride, methanol, isopropyl alcohol, and various combinations and ratios thereof.

One method of preparation for the compounds used for the subject invention involves extraction from marine sponges of the order Halichondrida (Phylum Porifera, Class Demospongiae) which is a problematic taxonomic group, with generic distinctions not clearly defined. Four samples used in connection with this invention have been assigned to the genus Spongosorites, Topsent 1896, a genus characterized by: a distinct and thick (up to 1 mm) dermal layer of smaller spicules arranged tangentially to the surface; a confused choanosomal arrangement of spicules with sporadic vague spicule tracts running parallel to the surface; bright-yellow color when alive, turning brown or black when preserved in alcohol; and two or three size categories of straight or crooked oxea. Spongosorites sp.1 (4-XII-84-1-22, black in alcohol) has crooked oxea and is distinguished in association with vermetids (Phylum Mollusca, Class Gastropoda); Spongosorites sp.3 (4-XII-84-1-23 and 23-VIII-85-1-39, tan-brown in alcohol) has fusiform straight oxea. Voucher samples are deposited in the Indian River Coastal Zone Museum of Harbor Branch Oceanographic Institution at Fort Pierce, Fla.

A current taxonomic identification of the sponge from which the compound dragmacidin was extracted is: Phylum Porifera, Class Demospongiae, Order Axinellida, Family Axinellidae, Genus Dragmacidon, as disclosed in U.S. Pat. No. 4,895,844.

The sponge Dragmacidon sp. is dark brown, both alive and preserved in ethanol. The consistency is brittle and non-compressible. The ectosome is a heavy organic skin with foreign material. The choanosome is fibrous, with sparse dendriticplumose spicule tracts. Spicules are trichodragmata and styles, 400–520 μm in length by 7–10 μm in width.

Identification of the sponge to the family Axinellidae and genus Dragmacidon is based on microscopic examination of a taxonomic voucher specimen. A similar voucher specimen is deposited at the Indian River Coastal Zone Museum (Catalog No. 003:00039), Harbor Branch Oceanographic Institution, Inc., Fort Pierce, Fla. (HBOI/DBMR number 2-VI-84-3-15). The sponge in the voucher specimen is preserved in 70% ethanol with an expected shelf life of at least 30 years and is accessible to those skilled in the art for identification purposes.

The sponge Dragmacidon sp. was collected from southeast Grand Bahama Island (latitude 26°28.75'N, longitude 77°53.50'W) at a depth of 480 ft. on a rock and sand slope.

As disclosed herein, a novel use for the described compounds is their use as an agent in the control of an inflammatory response. For purposes of the subject invention, it will be understood by those of ordinary skill in the art that the terms "inflammation" and "inflammatory response" refer to any and all such inflammatory cellular and tissue reactions including, but not limited to, immune-related responses and/or allergic reactions to a physical, chemical, or biological stimulus. "Anti-inflammatory activity," as used herein, will be understood by those of ordinary skill in the art to mean biological activity inhibiting or controlling any inflammatory response. Anti-inflammatory activity can occur by modes of action which can include, but are not limited to, lipid-mediated inflammatory responses, e.g., (i) suppression of cellular activation of phospholipase A2, either directly (as is known for the anti-inflammatory compound, manoalide) or indirectly (as is known for the anti-inflammatory compound, hydrocortisone); (ii) by inhibiting, or controlling, cyclooxygenation of arachidonic acid, similar to the action of non-steroidal anti-inflammatory drugs; or (iii) by affecting lipooxygenase products of peroxidase reactions to arachidonic acid, or by non-lipid-mediated inflammatory responses, e.g., protease-induced inflammatory responses, and the like.

Following are examples which illustrate procedures, including the best mode, for practicing the invention. These examples should not be construed as limiting. All percentages are by weight and all solvent mixture proportions are by volume unless otherwise noted.

Example 1—Preparation of Topsentin and Bromotopsentin

The frozen sample (264 g) of marine sponge, *Spongosorites ruetzleri* (Van Soest and Stentoft 1988), collected at a depth of 1149 feet at Goulding's Cay, Bahamas, was extracted twice with methanol-toluene (3:1). The combined extracts on concentration on a water bath at 30° C. in vacuo gave as a residue (11.32 g) of crude extract which was partitioned between pentane and 10% aqueous methanol. The alcohol layer was then diluted to 30% water and extracted with $CH_2Cl_2$. The aqueous methanol layer was concentrated and partitioned between butanol and water. A portion (200 mg) of the *Herpes simplex* virus type 1 (HSV-1)-active, butanol-soluble fraction was dissolved in 20% aqueous methanol (1 ml) and chromatographed on a column (ID= 22 mm; height=40 mm) packed with reversed-phase material (Amicon silica-C8, 20–45 μm). The active fraction (123 mg) was eluted with 20% aqueous methanol and purified by reversed-phase HPLC (IBM 5μ C18, 10 mm×250 mm, 20% aqueous methanol) to yield pure topsentin I(a), 20 mg, and bromotopsentin I(b), 67 mg as yellow powder.

Topsentin, amorphous, bright-yellow solid, mp>250° C. when analyzed by conventional methods and apparatus, produced the following spectral data:

UV absorption, $\lambda_{max}$ (MeOH) 208 nm ($\epsilon$12,000), 246 sh (5100), 285 (4500), and 375 (4600);

IR (KBr) 3395, 3275, 1635, 1590, 1530, 1455, 1270, 1165, 1115, 1095, 1005, and 876 $cm^{-1}$;

$^1$H NMR (360 MHz, DMSO-$d_6$+1% TFA-H) 6.841 (1H, dd, J=8.6, 1.8 Hz), 6.997 (1H, d, J=1.8 Hz), 7.201 (2H, m), 7.523 (1H, d, J=7.9 Hz), 7.990 (1H, d, J=7.6 Hz), 8.041 (1H, d, J=8.6 Hz), 8.155 (1H, d, J=2.8 Hz), 8.159 (1H, s), 8.487 (1H, d,=3.2 Hz), 11.762 (1H, s), 12.355 (1H, d, J=2.2 Hz);

$^{13}$C NMR (90 MHz, DMSO+1% TFA-H) 98.11 (d), 102.72 (s), 113.12 (d), 113.95 (s), 116.00 (d), 118.67 (s), 119.46 (d), 120.50 (d), 122.02 (d), 122.44 (d), 124.27 (s), 125.74 (d), 131.11 (s), 136.53 (s), 137.78 (d), 138.33 (s), 141.23 (s), 155.25 (s), 171.5 (s);

EIMS 342 (100%, $C_{20}H_{14}N_4O_2$, $M^+$), 209 (39, $C_{12}H_7N_2O$), 183 (28, $C_{11}H_9N_3$), 171 (17, $C_{10}H_7N_2O$), 160 (145, $C_9H_7N_2O$), 133 (65, $C_8H_7$ NO), and 105 (15).

Bromotopsentin, yellow crystals, m.p. 296°–297° C., when analyzed by conventional methods and apparatus, produced the following spectral data:

UV absorption, $\lambda_{max}$ (MeOH) 209 nm ($\epsilon$13,000), 236 (9700), 287 (5000), and 374 (5800);

IR (KBr) 3400–3100, 2255, 2120, 1635, 1590, 1520, 1445, 1265, 1230, 1165, 1028, 1005, and 875 $cm^{-1}$;

$^1$H NMR (360 MHz, $CDCl_3$:$CF_3COOH$: 1:1) 7.098 (1H, dd, J=8.6, 2.4 Hz), 7.193 (1H, d, J=2.4 Hz), 7.227 (1H, dd, J=8.6, 1.8 Hz), 7.558 (1H, dd, J=8.6 Hz), 7.668 (1H, d, J=1.8 Hz), 7.824 (1, s), 7.927 (1H, d, J=3 Hz), 8.202 (1H, d, J=8.6 Hz), 8.371 (1H, d, J=3 Hz), 9.272 (1H, brs), 10.409 (1H, brs);

$^{13}$C NMR (90 MHz, $CDCl_3$:$CF_3COOH$:1:1) 101.6 (d), 103.7 (s), 116.7 (d), 117.0 (s), 117.5 (d), 118.2 (d), 119.6 (s), 121.5 (d), 122.6 (s), 125.2 (s), 125.5 (d), 127.7 (d), 128.0 (d), 135.0 (s), 139.7 (s), 140.5 (s), 140.8 (d), 141.7 (s), 155.0 (s), 172.4 (s);

EIMS 422/420 (40%, $C_{20}H_{13}BrN_4O_2$, $M^+$), 394/392 (1.3, $C_{19}H_{11}$ $BrN_3O_2$), 342 (13, $M^+$-Br), 289/287 (6%, $C_{12}H_7BrN_3O$), 263/261 (100, $C_{11}H_8$ $BrN_3$), 223/221 (13, $C_9H_6BrN_2$), 209/207 (9.5, $C_9H_6BrNO$), 182 (15, 261-Br), and 133 (94, $C_8H_7NO$).

Example 2—Preparation of a Deoxybromotopsentin and Other Related Analogs and Derivatives Frozen sponge sample of Spongosorites sp.3 collected at Goulding's Cay, Bahamas at-229 m was homogenized and steeped repeatedly in methanol and 10% toluene followed by methanol. The alcohol layer was concentrated and re-partitioned between 1-butanol and water, and the butanol-soluble fraction was vacuum chromatographed over RP material (Amicon, silica gel C18, 20–45 μm) using 20% aqueous methanol. The yellow fraction was then subjected twice to RP-HPLC (C18, 5 μm, 20% water in MeOH) to give bromotopsentin I(b) and 4,5-dihydro-6"-deoxybromo-topsentin. 4,5-dihydro-6"-deoxybromotopsentin is a yellow powder with the following spectral data:

$[\alpha]^{24}D$ 198° (c 2.0, MeOH)

UV (MeOH) $\lambda_{max}$ nm 328 ($\epsilon$5700), 274 (8800), 214 (34,000), 198 (29,500);

IR (KBr) 3630, 3390, 3280, 2920, 2860, 1664, 1570, 1450, 1420, 1332, 1240, 1160, 1120, 1100, 1020, 950, 805, and 750 $cm^{-1}$;

LREIMS m/z (tel. intensity) 406 (95), 404 (100), 378 (41), 376 (39), 326 (10), 298 (6), 297 (7), 291 (10), 289 (9), 235 (6), 233 (6), 210 (12), 208 (10), 197 (10), 195 (10), 189 (5), 156 (12), 155 (19), 144 (28), 130 (14).

$^1$H and $^{13}$C NMR collected data also supported the structure given above.

Calcd for $C_{20}H_{13}^{79}BrN_4O$:404.0272 (M-2H). Found 404.0300 (HREIMS). The conversion of bromotopsentin to topsentin; the preparation of 3-(hydroxyacetyl)indole, 3-chloroacetyl-6-(benzyloxy)indole, and 3-hydroxyacetyl-6-(benzyloxy)indole as synthons; the synthesis directly from (hydroxylacetyl)indoles of O-benzyltopsentin, O-benzyliso-topsentin, O,O'-dibenzylhydroxytopsentin, and deoxytopsentin I(e); the preparation of compounds I(e) and O-benzyltopsentin, O-benzylisotopsentin, and O,O'-dibenzyldihydroxytopsentin from isolated glyoxal intermediates; the conversion of O-benzyltopsentin to topsentin I(a); the conversion of O-benzylisotopsentin to isotopsentin I(e); the synthesis of hydroxytopsentin I(d) from 3-hydroxy-acetyl-6-(benzyloxy)-indole; preparation of 3-chloroacetyl-5-benzyl(oxy)indole; the preparation of 3-hydroxyacetyl-5-(benzyloxy)indole; synthesis of neohydroxytopsentin I(h); and synthesis of neotopsentin I(f) and neoisotopsentin I(g) are described in U.S. Pat. No. 4,866,084, which has been incorporated herein by reference. Topsentin monoacetate III(k) and topsentin diacetate III(l) can also be converted from topsentin or its analogs by methods well known and readily available to those skilled in the art.

Example 3—Isolation of Nortopsentin A, B, & C

The sponge Spongosorites sp. (80 g), collected at the depth of 630 ft. off Chub Cay, Bahamas, on Aug. 26, 1985, was lyophilized and extracted with methanol-toluene (3:1). The extract was evaporated to dryness and partitioned between ethyl acetate and water. The water soluble fraction was further partitioned with butanol. The combined ethyl acetate and butanol fractions were chromatographed on a Hibar LiChrosorb $NH_2$ column using HPLC with $CHCl_3$-MeOH (5:1) as elution solvent to yield a semi-purified compound, nortopsentin B (3 mg).

Sponge of the genus Halichondria (830 g) was collected at the depth of 1512 ft. off Nassau, Bahamas, on Mar. 15, 1987. The frozen sponge was extracted with 1.5 l of methanol four times. The extracts were combined and concentrated under reduced pressure to give a 400 ml of water suspension, which was then extracted with ethyl acetate (300 ml×3). The resulting ethyl acetate fraction was evaporated to dryness to yield a crude fraction (12.02 g). It was found that the majority of the components in this fraction was topsentin and bromotopsentin.

A two-phase solvent system was generated by mixing heptane, ethyl acetate, methanol, and water in a ratio of 4:7:4:3. The crude fraction (12.00 g) was partitioned between 150 ml of the upper phase solvent and 300 ml of the lower phase solvent. The resulting lower layer fraction was extracted with 150 ml of the upper phase solvent three more times. The combined upper layer fractions were evaporated to dryness (5.75 g) and dissolved in 50 ml of the upper phase solvent. The solids were filtered off and the eluant was evaporated to dryness (4.46 g). The residue was dissolved again in 30 ml of the upper phase solvent. After removal of the insoluble material and evaporation of the solvent, 2.75 g of a solid was obtained.

This solid was further fractionated by using centrifugal countercurrent chromatography with two different solvent systems consisting of heptane/ethyl acetate/methanol/water in ratios of 4:7:4:3 and 5:7:4:3. A fraction containing nortopsentin A and a mixture of nortopsentin B and C along with topsentin (400 mg) and bromotopsentin (540 mg) were obtained. Nortopsentin A (250 mg) was purified by HPLC on a Hibar $NH_2$ column (10×250 mm), using 5:1 chloroform/methanol as eluant. Preparative TLC (Kieselgel $60F_{264}$, 2 mm thickness, ethyl acetate) afforded a pure nortopsentin C (200 mg) and a fraction containing nortopsentin B. Pure nortopsentin B (250 mg) was finally recrystallized from ethyl acetate/chloroform.

Example 4—Extraction and Isolation of Hamacanthins

A freshly thawed Hamacantha sp. sponge (223 g, wet weight) was extracted three times with EtOH. The concentrated extract was then partitioned between EtOAc and $H_2O$. The EtOAc soluble fraction (1.2 g) showed activity against C. albicans (MIC=3.1 μg/ml; RPMI-1640 growth medium). This active fraction was chromatographed on Si gel (Kiesel gel 60 H) using $CH_2Cl_2$/MeOH step gradient. The antifungal active fraction (70 mg, C. albicans MIC=1.6 μg/ml; RPMI-1640) that eluted with 2% MeOH/$CH_2Cl_2$ on HPLC (Si gel, 5 μ, 250×10 mm) with 2.5% MeOH/$CH_2Cl_2$ gave hamacanthin A and hamacanthin B as the active components.

Hamacanthin A. Pale yellow power (22 mg, 0.011% from frozen sponge); $[a]^{24}D$ 84° (c=0.1 MeOH); ir (neat) 3225 broad, 2294, 1672, 1585, 1437 $cm^{-1}$; uv λ max (MeOH) 219 nm (☐76500), 280 (20600), 325 (13300); hrfabms (nitrobenzyl alcohol) m/z 486.9605, Δ 1.2 mmu for $C_{20}H_{15}{}^{79}Br^{81}BrN_4O$ (M+H); lrfabms (nitrobenzyl alcohol) m/z (rel. int.) 489 (18), 487 (36), 485 (21), 460 (11), 307 (100), 289 (55), 245 (98). NMR data is shown in Table 1.

Hamacanthin B. Pale yellow powder (27 mg, 0,014%); $[\alpha]^{24}D$ 172° (c=0.1 MeOH); ir (neat) 3250 (broad), 2925, 1672, 1585, 1437 $cm^{-1}$; uv λ max (MeOH) 219 nm (ε76500), 280 (20600), 325 (13300); hrfabms (nitrobenzyl alcohol) m/z 486.9606, Δ1.3 mmu for $C_{20}H_{15}{}^{79}Br^{81}BrN_4O$ (M+H); lrfabms (nitrobenzyl alcohol) m/z (rel. int.) 489 (40%), 487 (88), 483 (43), 460 (13), 429 (17), 307 (100), 289 (60), 245 (60). NMR data is shown in Table 1.

TABLE 1

$^{13}C$- and $^1H$ NMR data[a] for hamacanthin A and hamacanthin B in DMSO-$d_6$

| | Hamacanthin A | | HMBC | Hamacanthin B | |
|---|---|---|---|---|---|
| | $^{13}C^b$ | $^1H^c$ | ($^1H$) | $^{13}C$ | $^1H$ |
| 1 | | 878(d, 1.0) | | | 8.49(t, 1.5) |
| 2 | 157.4[d] | | H1 | 157.2 s | |
| 3 | 157.6 s | | H5, H2' | 157.0 s | |
| 5 | 53.4 t | 4.05(dd, 16.2, 5.1) | H1, H6 | 53.6 d | 5.25(dd, 9.5, 4.8) |
| | | 4.10(dd, 16.2, 8.5) | | | |
| 6 | 46.1 d | 4.98(ddd, 8.5, 5.1, 1.0) | H1, H5, H2" | 43.2 t | 3.47(ddd, 12.9, 9.5, 1.0) |
| | | | | | 3.61(ddd, 12.9, 4.8, 1.5) |
| 1' | | 11.59(d, 2.7) | | 11.62 s | |
| 2' | 132.6 d | 8.41(d, 2.7) | | 132.7 d | 8.41 (s) |
| 3' | 111.0 s | | H1', H2' | 111.0 s | |
| 3a' | 125.0 s | | H2', H5', H' | 125.0 s | |
| 4' | 124.1 d | 8.29(d, 8.5) | | 124.1 d | 8.30(d, 8.7) |
| 5' | 123.2 d | 7.20(dd, 8.5, 2.0) | H7' | 123.3 d | 7.17(dd, 8.7, 1.6) |

TABLE 1-continued $^{13}$C- and $^1$H NMR data[a] for hamacanthin A and hamacanthin B in DMSO-$d_6$

| | Hamacanthin A | | HMBC | Hamacanthin B | |
|---|---|---|---|---|---|
| | $^{13}$C[b] | $^1$H[c] | ($^1$H) | $^{13}$C | $^1$H |
| 6' | 114.7 s | | H4' | 114.8 s | |
| 7' | 114.2 d | 7.62(d, 2.0) | H5' | 114.1 d | 7.63(d, 1.6) |
| 7a' | 137.0 s | | H2', H4' | 136.9 s | |
| 1" | | 11.15(d, 2.3) | | 11.12 s | |
| 2" | 124.5 d | 7.30(d, 2.3) | H6 | 123.6 d | 7.28(s) |
| 3" | 113.1 s | | H5, H6, H1" | 114.8 s | |
| 3a" | 124.6 s | | H2", H5", H7" | 125.0 s | |
| 4" | 120.7 d | 7.66(d, 8.5) | | 120.8 d | 7.65(d, 8.6) |
| 5" | 121.5 d | 7.13(dd, 8.5, 2.0) | H7" | 121.4 d | 7.13(dd, 8.6, 1.6) |
| 6" | 114.7 s | | H4" | 113.9 s | |
| 7" | 114.2 d | 7.56(d, 2.0) | H5" | 114.2 d | 7.59(d, 1.6) |
| 7a" | 137.2 s | | H1", H2" | 137.2 s | |

[a]Table entries are chemical shift, ppm from solvent (multiplicity, J in Hz).
[b]Assignments based on APT, DEPT, and HMQC experiments.
[c]Assignments based on COSY and TOCSY experiments.
[d]Assignment based on a SINEPT experiment.

Example 5—Anti-Inflammatory Properties of the Bis-Indole Compounds

The anti-inflammatory activity of a particular compound can be demonstrated by two standard assays, one in vivo and one in vitro. These assays are commonly employed by those skilled in the art and are accepted as indicative of anti-inflammatory activity in humans. These assays are described below.

A. Mouse ear anti-inflammatory assay. The test compound and a known inflammatory agent, phorbol myristate acetate (PMA), are topically applied simultaneously to the left ears of mice. Three hours and 20 minutes following application, the mice are sacrificed. Both left and right ears are removed and standard-sized bores taken. Edema (inflammation) is measured as the difference in weight between left and right ears (Van Arman, C. G. [1974] *Clin. Pharmacol. Ther.* 16:900–904).

B. In vitro inactivation of bee venom phospholipase A2. Phosphatidylcholine dipalmitoyl (labeled and unlabeled) is used as the substrate in monomolecular form. Test compounds are preincubated with the enzyme (25 units/0.5 ml) for 1 hour at 41° C. The reaction is initiated by the addition of an aliquot of the drug-enzyme mixture to the substrate (0.68 μmoles/0.5 ml) and allowed to continue for 15 seconds. The reaction is terminated and the hydrolysis product is measured via scintillation counting. For screening, the test compounds (in methanol or DMSO) are added to the enzyme at a standard bench concentration of 5 mg/ml, for an enzyme-incubation concentration of 80 μg/ml, and a final concentration of 0.8 μg/ml. Assays are done in triplicate and results are averaged and compared to a vehicle control rate of hydrolysis.

The bis-heterocycle compounds of the subject invention, e.g., the bis-indole compounds, show significant anti-inflammatory properties. When screened for the ability to reduce edema in mouse ears caused by application of a known inflammatory agent, phorbol myristate acetate, topsentin was found to have greater potency than to the known anti-inflammatories hydrocortisone, indomethacin, and manoalide (see Table 2).

TABLE 2

Relative potency of topsentin, manoalide, Indomethacin, and hydrocortisone in the topical inhibition of PMA-induced mouse ear edema

| Compound | $ED_{50}$ (μg/ear) |
|---|---|
| Hydrocortisone | 20 |
| Indomethacin | 250 |
| Manoalide | 100 |
| Topsentin | 15 |

In addition, bis-indole compounds were tested for percent inhibition of PMA-induced edema. Topsentin, bromotopsentin, dragmacidin, nortopsentin A, and nortopsentin C displayed significant potency (Table 3). Topsentin monoacetate and diacetate showed moderate activity in this assay.

TABLE 3

Percent inhibition of PMA induced edema in mouse ears by topsentin and analogs

| Compound Name | Compound Number | Dose | % Inhibition of edema |
|---|---|---|---|
| Topsentin | HB 18 | 50 μg/ear | 70.6 |
| Bromotopsentin | HB 19 | 50 μg/ear | 75.4 |
| Topsentin monoacetate | | 50 μg/ear | 45.8 |
| Topsentin diacetate | | 50 μg/ear | 42.6 |
| Dragmacidin | HB 6 | 50 μg/ear | 64.0 |
| Nortopsentin A | HB 127 | 50 μg/ear | 98.1 |
| Nortopsentin B | HB 128 | 50 μg/ear | 38.2 |
| Nortopsentin C | HB 129 | 50 μg/ear | 70.1 |
| Hamacanthin A | HB 191 | 50 μM | 50.0 |
| Hamacanthin B | HB 192 | 50 μM | 34.0 |

Topsentin also proved to be capable of the inactivation of bee venom phospholipase A2 (Table 4). Hydrocortisone and indomethacin were inactive at concentrations up to 1 mM.

TABLE 4

Relative potency of topsentin, manoalide, indomethacin, and hydrocortisone in the inactivation of bee venom phospholipase A2

| Compound | $IC_{50}$ |
| --- | --- |
| Hydrocortisone | >1 mM |
| Indomethacin | >1 mM |
| Manoalide | 0.05 μM |
| Topsentin | 0.5 μM |

Bis-indole compounds of the subject invention were tested at a final concentration of 1 μM for their percent inactivation of the bee venom phospholipase A2. The results of these tests are shown in Table 5.

TABLE 5

Percent inactivation of bee venom phospholipase A2 by topsentin and analogs

| Compound Name | Compound Number | Final Concentration | % Inactivation |
| --- | --- | --- | --- |
| Topsentin | HB 18 | 1 μM | 67 |
| Bromotopsentin | HB 19 | 1 μM | 33 |
| Topsentin monoacetate | | 1 μM | 42 |
| Topsentin diacetate | | 1 μM | 32 |
| Dragmacidin | HB 6 | 1 μM | 27 |
| Nortopsentin A | HB 127 | 1 μM | 30 |
| Nortopsentin B | HB 128 | 1 μM | 27 |
| Nortopsentin C | HB 129 | 1 μM | 26 |
| Hamacanthin A | HB 191 | 1.6 μM | 37 |
| Hamacanthin B | HB 192 | 1.6 μM | 32 |

In consideration of the data presented, the subject bis-indole compounds have been shown to have potent anti-inflammatory characteristics with unique clinical applications. Their mechanism of action appears to be the consequence of inactivation of phospholipase A2.

Figure 2:
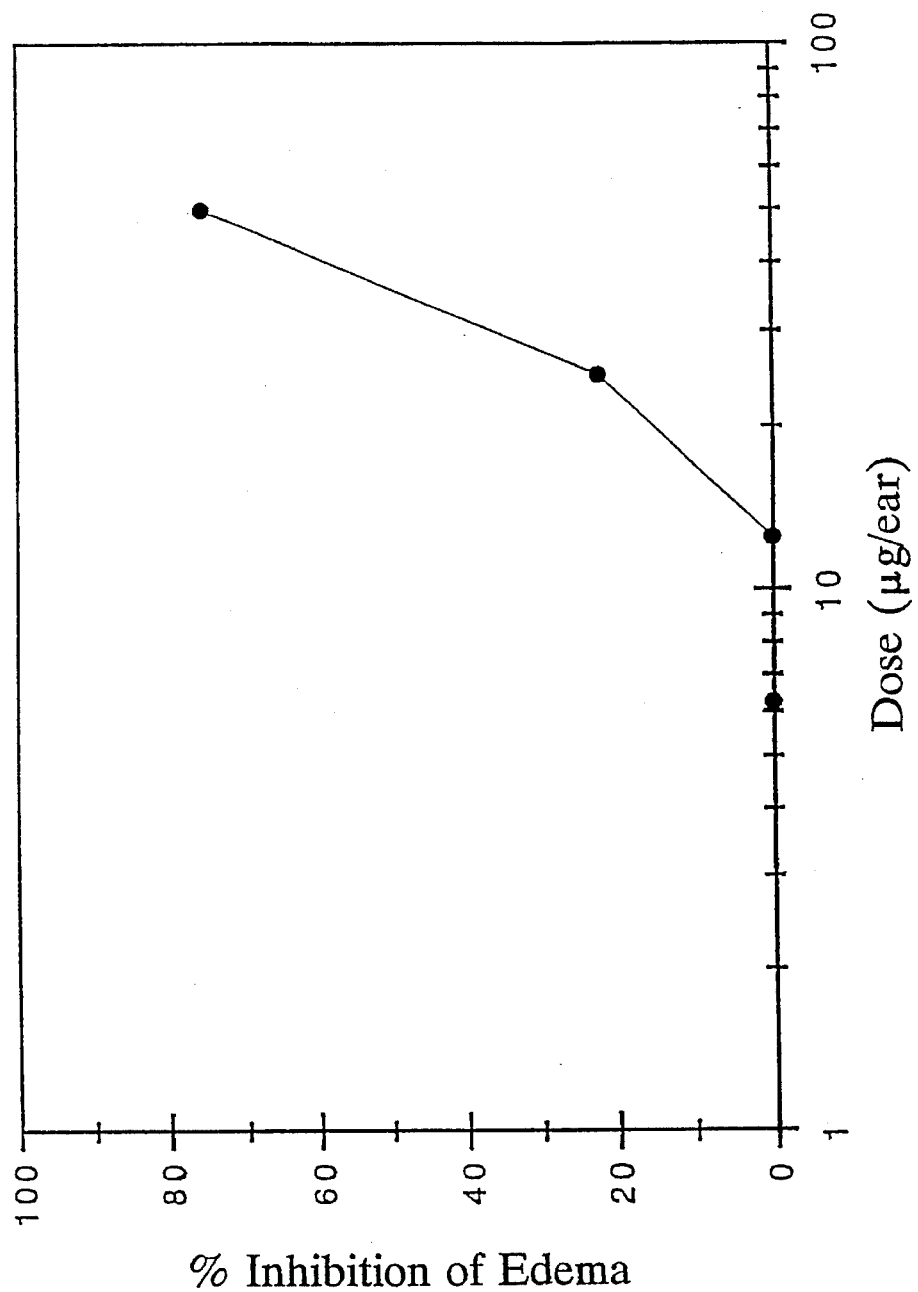
FIG. 2 shows the dose response for topsentin (HB18), as measured by percent inhibition of edema in the mouse ear anti-inflammatory assay.
Figure 3:
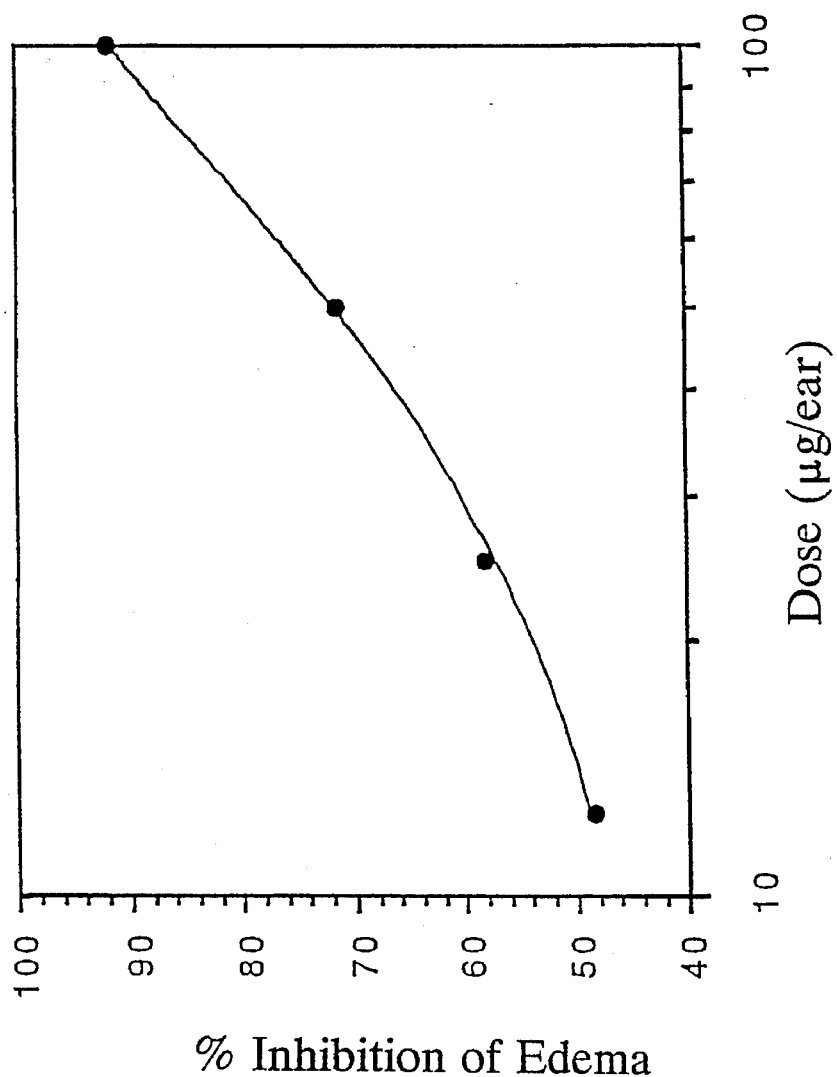
FIG. 3 shows the dose response for bromotopsentin (HB19), as measured by percent inhibition of edema in the mouse ear anti-inflammatory assay.

Dose-response curves for topsentin and bromotopsentin were generated and are shown as FIGS. 1, 2, and 3. Specifically, the dose-response curve for topsentin, measured as percent inactivation of bee venom phospholipase A2 (FIG. 1) shows up to 80% inactivation at a final concentration of approximately 2 μM. In the mouse ear edema inhibition assay, a dose of about 12 μg/ear of topsentin achieved nearly 50% inhibition of edema, and doses of 100 μg/ear showed more than 90% inhibition of edema (FIG. 2). Similarly, percent inhibition of mouse ear edema by bromotopsentin ranged from about 20% inhibition for a dose of approximately 25 μg/ear to about 75% inhibition at a dose of 50 μg/ear.

Example 6—Formulation and Administration

The compounds of the invention are useful for various non-therapeutic and therapeutic purposes. It is apparent from the testing that the compounds of the invention are effective for immunomodulation, antiviral activity, and for controlling tumor growth. The compounds can be used to inhibit unwanted viral growth in the work areas of virology labs. Also, the compounds can be used as ultraviolet screeners in the plastics industry since they effectively absorb UV rays. As disclosed herein, they can be used therapeutically for treating tumors, or as immunomodulatory or antiviral agents in animals and humans.

Therapeutic application of the new compounds and compositions containing them can be contemplated to be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the infection, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as active ingredient, an effective amount of one or more of the subject compounds and one or more non-toxic, pharmaceutically acceptable carriers or diluents can be used by persons of ordinary skill in the art. In addition, the pharmaceutical composition can comprise one or more of the bis-heterocycle compounds, e.g., a bis-indole, as a first active ingredient plus a second active ingredient comprising an anti-inflammatory compound known in the art. Such known anti-inflammatory drugs include, but are not limited to, the steroidal anti-inflammatory drugs and the non-steroidal anti-inflammatory drugs (NSAIDs).

In accordance with this invention, pharmaceutically effective amounts of a known anti-inflammatory agent and the bis-heterocycle compounds are administered sequentially or concurrently to the patient. The most effective mode of administration and dosage regimen of bis-heterocycle compounds and anti-inflammatory agent will depend upon the type of disease to be treated, the severity and course of that disease, previous therapy, the patient's health status, and response to bis-indoles and the judgment of the treating physician. Bis-heterocycle compositions may be administered to the patient at one time or over a series of treatments.

Preferably, the bis-heterocycle, e.g., a bis-indole composition, and the second anti-inflammatory agent are administered sequentially to the patient, with the anti-inflammatory agent being administered before, after, or both before and after treatment with the bis-indole compound. Sequential administration involves treatment with the anti-inflammatory agent at least on the same day (within 24 hours) of treatment with bis-indole and may involve continued treatment with the anti-inflammatory agent on days that the bis-indole is not administered. Conventional modes of administration and standard dosage regimens of anti-inflammatory agents may be used (see Gilman, A. G. et al. [eds.] *The Pharmacological Basis of Therapeutics*, pp. 697–713, 1482, 1489–91 [1980]; *Physicians Desk Reference*, 1986 Edition). For example, indomethacin can be administered orally at a dosage of about 25–50 mg, three times a day. Higher doses can also be used. Alternatively, aspirin (about 1500– 2000 mg/day), ibuprofen (about 1200–3200 mg/day), or conventional therapeutic doses of other anti-inflammatory agents can be used. Dosages of anti-inflammatory agents can be titrated to the individual patient.

According to one embodiment of this invention, the patient may receive concurrent treatments with the anti-inflammatory agent and compositions comprising bis-heterocycles, e.g., bis-indoles. For example, local, intralesional, or intravenous injection of bis-indoles is preferred (see Gilman et al., supra at pp. 1290–91). The anti-inflammatory agent should preferably be administered by subcutaneous injection, subcutaneous slow-release implant, or orally.

Alternatively, the patient can receive a composition comprising a combination of one or more bis-indole compounds and an anti-inflammatory agent according to conventional modes of administration of agents which exhibit antibacterial, anticancer, antitumor, or anti-inflammatory activity. These include, for example, parenteral, subcutaneous, intravenous, or intralesional routes of administration.

The compositions used in these therapies can also be in a variety of forms. These include, for example, solid, semi-solid, and liquid dosage forms, such as tablets, pills, powders, liquid solutions or suspension, suppositories, injectable and infusible solutions. The preferred form depends on the intended mode of administration and therapeutic application. The compositions also preferably include conventional pharmaceutically acceptable carriers and adjuvants which are known to those of skill in the art. Preferably, the compositions of the invention are in the form of a unit dose and will usually be administered to the patient one or more times a day.

The compounds of the subject invention may also be administered utilizing liposome technology, slow release capsules, implantable pumps, and biodegradable containers. These delivery methods can, advantageously, provide a uniform dosage over an extended period of time.

Examples of such carriers or diluents include ethanol, dimethyl sulfoxide, glycerol, silica, alumina, starch, and equivalent carriers and diluents. While effective amounts may vary, as conditions in which compositions are used vary, a minimal dosage required for anti-inflammatory activity is generally between 0.01 and 100 µg of the compound. To provide for the administration of such dosages for the desired therapeutic treatment, new pharmaceutical compositions of the invention will advantageously comprise between about 0.1% and 45%, and especially, 1 and 15% by weight of the total of one or more of the new compounds based on the weight of the total composition including carrier or diluent.

Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Once improvement of the patient's condition has occurred, a maintenance dose is administered if necessary. Subsequently, the dosage or the frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of disease symptoms.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A compound selected from the group consisting of hamacanthin A, hamacanthin B, or a pharmaceutical acceptable salt thereof.

2. The compound, according to claim 1, wherein said compound is hamacanthin A.

3. The compound, according to claim 2, wherein said compound is hamacanthin B.

* * * * *

UNITED STATES PATENT AND TRADEMARK OFFICE
CERTIFICATE OF CORRECTION

PATENT NO. : 5,496,950

DATED : March 5, 1996

INVENTOR(S) : Oliver J. McConnell, Gabriel Saucy, Robert Jacobs, Sarath P. Gunasekera It is certified that error appears in the above-indentified patent and that said Letters Patent is hereby corrected as shown below:

Column 1: line 17: "his-heterocyclic" should read --bis-heterocyclic--.

Column 4: line 45:

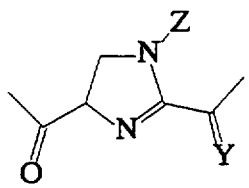 should read 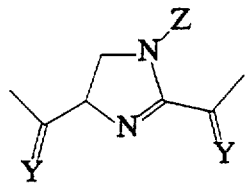

Column 6: line 35:

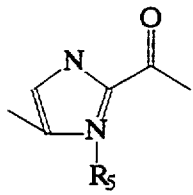 should read 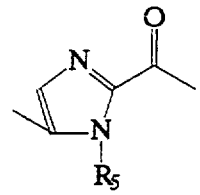

Column 9: line 38: "in vacuo" should read --*in vacuo*--; line 65: "(1H, d,=3.2 Hz)" should read --(1H, d, J=3.2 Hz)--.

UNITED STATES PATENT AND TRADEMARK OFFICE
CERTIFICATE OF CORRECTION

PATENT NO. : 5,496,950

DATED : March 5, 1996

INVENTOR(S) : Oliver J. McConnell, Gabriel Saucy, Robert Jacobs, Sarath P. Gunasekera It is certified that error appears in the above-indentified patent and that said Letters Patent is hereby corrected as shown below:

Column 10: line 54: "(tel. intensity)" should read --(rel. intensity)--.

Column 11: line 6: "I(e);" should read --I(c);--; "diacetate HI(1)" should read --diacetate III(I)--.

Column 12: line 35: "(☐ 76500)" should read --($\epsilon$ 76500)--; "(27 mg, 0,014%);" should read --(27 mg, 0.014%);--; Column 12, Bottom, Table 1, line 1: "878(d,1.0)" should read --8.78(d,1.0)--.

Column 13: lines 28-29: "in vivo" should read --*in vivo*--; lines 28-29: "in vitro" should read --*in vitro*--; line 43: "in vitro" should read --*in vitro*--.

Signed and Sealed this

Third Day of September, 1996

BRUCE LEHMAN

Attest:

*Attesting Officer*              Commissioner of Patents and Trademarks